(12) United States Patent
Nambu et al.

(10) Patent No.: US 6,548,688 B1
(45) Date of Patent: Apr. 15, 2003

(54) DIAMMONIUM RUTHENIUM DIETHYLENETHRIAMINEPENTAACETATE OR HYDRATES THEREOF AND PROCESS FOR THE PREPARATION OF BOTH

(75) Inventors: Nobuyoshi Nambu, Yokkaichi (JP); Atsushi Nakamura, Yokkaichi (JP); Hiroshi Ito, Osaka (JP)

(73) Assignees: Chubu Chelest Co., Ltd., Osaka (JP); Chelest Corporation, Osaka (JP)

( * ) Notice: Subject to any disclaimer, the term of this patent is extended or adjusted under 35 U.S.C. 154(b) by 0 days.

(21) Appl. No.: 09/979,621

(22) PCT Filed: May 22, 2000

(86) PCT No.: PCT/JP00/03246

§ 371 (c)(1),
(2), (4) Date: Feb. 6, 2002

(87) PCT Pub. No.: WO00/71499

PCT Pub. Date: Nov. 30, 2000

(30) Foreign Application Priority Data

May 25, 1999 (JP) .............................. 11-145235

(51) Int. Cl.[7] .................................. C07F 15/00
(52) U.S. Cl. .................................... 556/136
(58) Field of Search ......................... 556/136

(56) References Cited

U.S. PATENT DOCUMENTS 5,676,923 A * 10/1997 Platzek et al. ........... 424/9.363

2002/0049190 A1 * 4/2002 Bridger et al. ............... 514/188

* cited by examiner

*Primary Examiner*—Porfirio Nazario-Gonzalez
(74) *Attorney, Agent, or Firm*—Smith Patent Office

(57) ABSTRACT

Diammonium ruthenium diethylenetriaminepentaacetate represented by formula (1) or hydrate thereof, which are water-soluble and excellent in handling and exhibit such high stability both in the air and in an aqueous solution as to withstand long-term storage. These novel compounds are useful as the catalyst for the synthesis of ammonia, the hydrogenation catalyst for carbonyl compounds or aromatic compounds, the raw material for the production of ruthenium-base metal oxide ceramics, and so on.

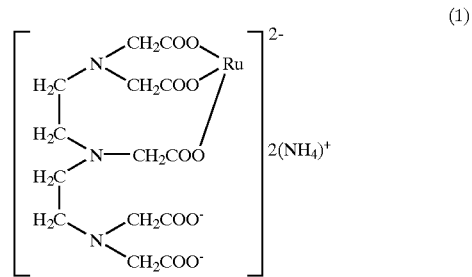

4 Claims, 2 Drawing Sheets

DIAMMONIUM RUTHENIUM DIETHYLENETHRIAMINEPENTAACETATE OR HYDRATES THEREOF AND PROCESS FOR THE PREPARATION OF BOTH

TECHNICAL FIELD

The present invention relates to novel ruthenium complex compounds, especially diammonium ruthenium diethylenetriaminepentaacetate or a hydrate thereof, which are water-soluble and stable both in the atmospheric condition and an aqueous solution, and a process for producing the both.

BACKGROUND ART

Ruthenium metal is a hard, brittle, silver-white and noble metal belonging to the platinum group. Currently, this metal is mainly obtained as a by-product when platinum is extracted from anode slime precipitated in an electrobath in a process for electrorefining nickel or copper. The ruthenium metal has been used for a corrosion-resistant protective metal layer, since it is insoluble in any acid in the absence of oxygen and excellent in corrosion resistance.

Ruthenium (IV) oxide [$RuO_2$], which is the most stable of ruthenium oxides, has the similar properties against acids to the ruthenium metal. Ruthenium is also known as an element having the effect of hardening platinum, palladium and the like. For instance, Pd-4.5% Ru alloy has been known as a noble metal for an ornament, Pt-10% Ru alloy as an ornamental metal or an electric contact material, and Os—Ru alloy as a material for a pen point of a fountain pen.

In addition, most of platinum group elements exhibit excellent catalytic activities for hydrogenation, oxidation, dehydrogenation and carbonylation. It has been known that ruthenium metal or complexes thereof also exhibit excellent catalytic activities for various reactions. For example, ruthenium metal has been proved to be sufficiently active as a catalyst for hydrogenation of inorganics such as ammonia synthesis and carbon monoxide, and hydrogenation of organics such as carbonyl compounds and aromatic compounds. Some ruthenium complexes also have been known as sufficiently active or selective catalysts for hydrogenation of an unsaturated bond, and others as a catalyst for hydrogenation using carbon monoxide.

Moreover, it has been known that ruthenium forms a variety of complexes and the typical examples includes a chloride of [$(NH_3)_5Ru^{III}$—O—$Ru^{IV}(NH_3)_4$—O—$Ru^{III}(NH_3)_5$]$^{6+}$, which is called ruthenium red. The chloride exhibits an intense red color when dissolved in water and, therefore, it is used for an oxidation-reduction indicator, dyeing of living tissue, and so on. In addition, since the usage in a semiconductor field is currently considered, it is expected that the demand grows increasingly in the future.

By the way, it has been known that most halides and complex compounds of the conventional ruthenium compounds are water-soluble. However, it is difficult to handle these halides because of the hygroscopic property. Moreover, since the halides are unstable in the aqueous solution, the halides are transformed into black hydrides due to the hydrolysis, or are decomposed into oxyhalides and hydrogen halides. Further, the complex compounds are generally not stable enough for long-term storage in the aqueous solution, although many of them are known to be stable in the air.

DISCLOSURE OF INVENTION

The present invention has been accomplished under these circumstances, and an object of the present invention is to provide novel ruthenium complex compounds or a hydrate thereof, which are water-soluble and excellent in handling and, moreover, stable both in the air and in an aqueous solution so as to withstand ling-term storage, and a process for producing the both.

According to an aspect of the present invention, the ruthenium complex compounds, which can achieve the aforementioned object, include diammonium ruthenium diethylenetriaminepentaacetate represented by the following formula (1) or the hydrate thereof.

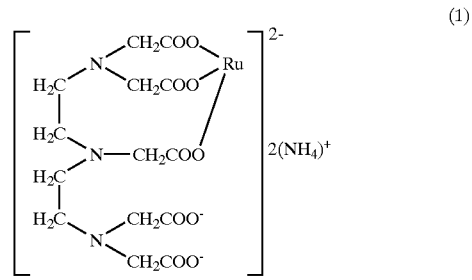

According to another aspect of the present invention, the process for producing the diammonium ruthenium diethylenetriaminepentaacetate represented by the above-mentioned formula (1) or the hydrate thereof includes conducting a solid-liquid reaction in an aqueous medium between diethylenetriaminepentaacetic acid and ruthenium salt which is water-soluble to obtain slurry, subjecting the slurry to a solid-liquid separation to remove a solid phase portion therefrom, and dissolving the solid phase portion into aqueous ammonia to obtain a complex compound. Alternatively, from the solution obtained by dissolving the solid phase portion into the aqueous ammonia, a hydrate of diammonium ruthenium diethylenetriaminepentaacetate may be crystallized so as to obtain the crystals of the hydrate thereof.

Further, the crystallized hydrate may be dried by heating, to obtain an anhydrate of the diammonium ruthenium diethylenetriaminepentaacetate.

BEST MODE FOR CARRYING OUT THE INVENTION

Under the above-mentioned circumstance, the inventors have been studying to provide ruthenium complex compounds which are water-soluble and excellent in stability both in the air and an aqueous solution, from various aspects of view, using a polyamino carboxylic acid chelating agent which easily forms chelate complexes stable particularly in the aqueous solution.

As a result, the inventors found that conducting a solid-liquid reaction in an aqueous medium between diethylenetriaminepentaacetic acid (hereinafter, referred to "DTPA") and water-soluble ruthenium salt (for example, ruthenium chloride, ruthenium bromide and other ruthenium halides) to produce DTPA-Ru complexes at a higher reaction ratio; and crystallizing the resulting DTPA-Ru complexes after adjusting pH thereof allow to obtain novel and crystalline ruthenium complex compounds which are water-soluble and stable both in the air and in the aqueous solution, and have accomplished the present invention.

The diammonium ruthenium diethylenetriaminepentaacetate of the present invention is the novel compound represented by the above-mentioned formula (1) and specified by the following constants.

Figure 1:
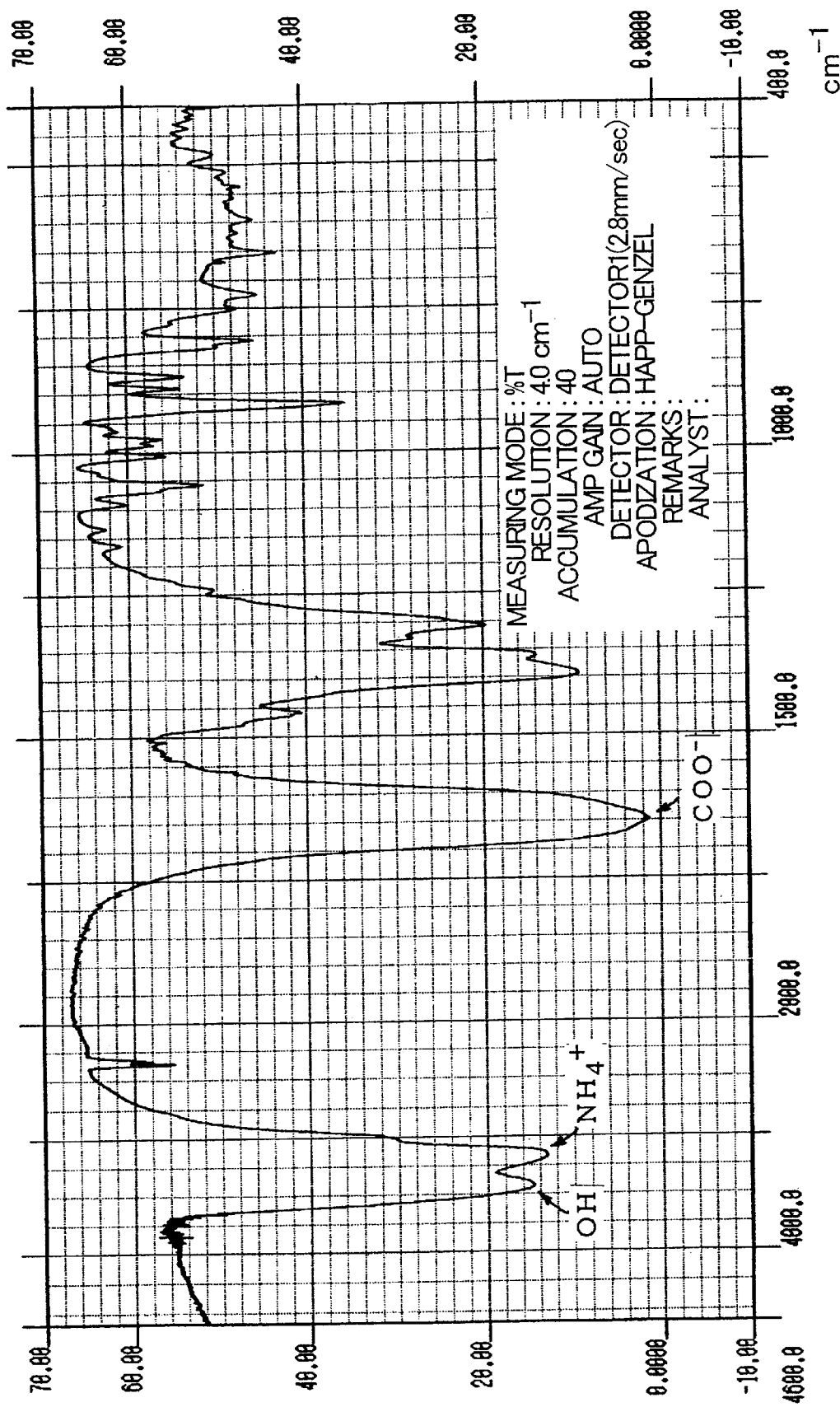
FIG. 1 is a chart showing an infrared absorption spectrum of diammonium ruthenium diethylenetriaminepentaacetate obtained in Example.
Figure 2:
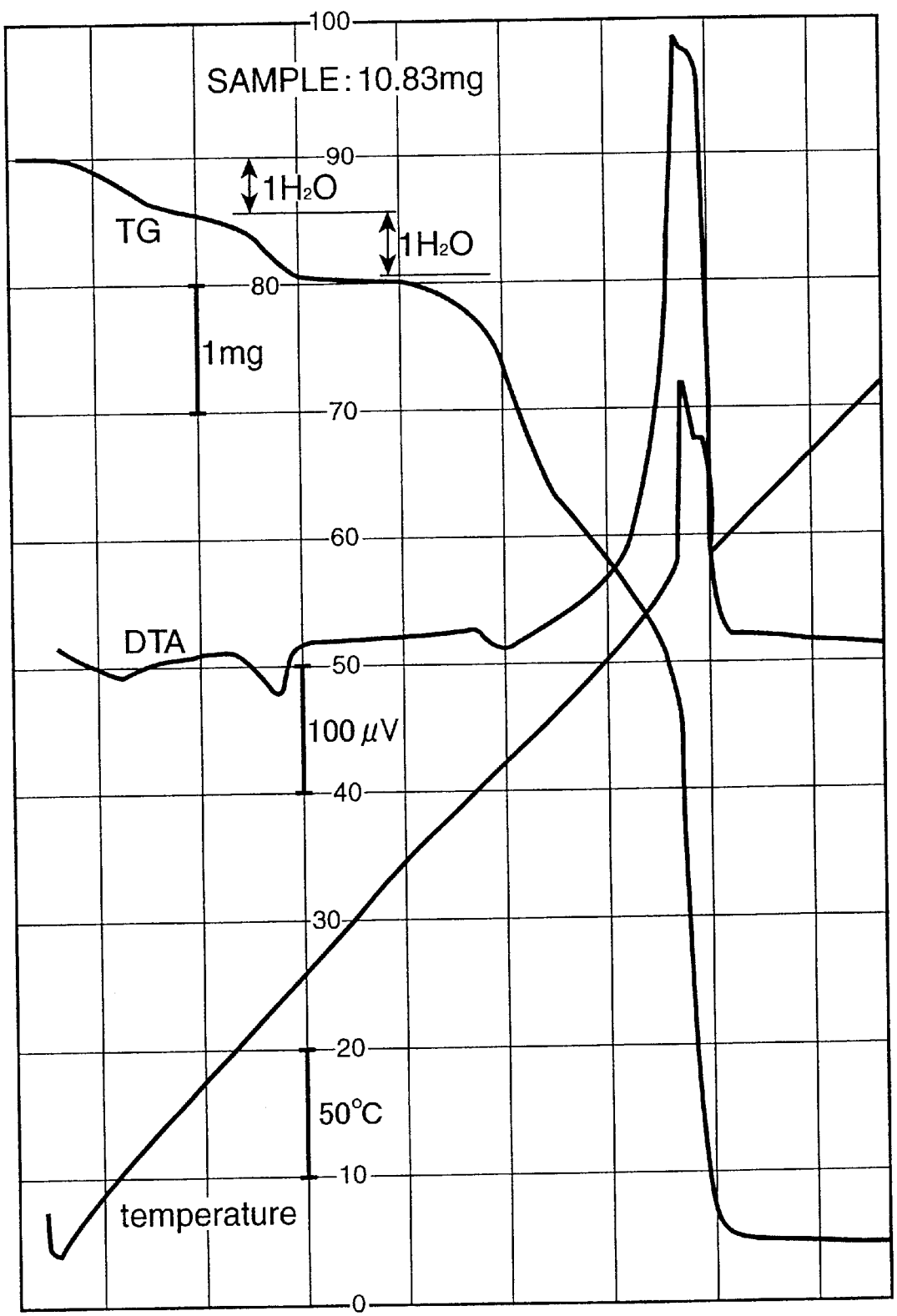
FIG. 2 is a chart showing a differential thermal analysis of the dihydrate of diammonium ruthenium diethylenetriaminepentaacetate obtained in Example.

(1) molecular weight: 561 (dihydrate)
(2) pH of 5% aqueous solution: 5.1
(3) solubility to water: 53 mass % (25° C.)
(4) melting point: 265° C. (decomposition)
(5) ruthenium content: 17.9 mass %
(6) infrared absorption spectrum (KBr): FIG. 1
(7) chart of differential thermal analysis(dihydrate): FIG. 2

The diammonium ruthenium diethylenetriaminepentaacetate of the present invention can be stably preserved not only in the atmospheric condition but also in the aqueous solution without being decomposed or transformed. Moreover, this compound does not precipitate in the aqueous solution, even when acid or alkali is added into the aqueous solution to change pH thereof, thus it is excellent in stability.

The inventive diammonium ruthenium diethylenetriaminepentaacetate or the hydrate thereof can be produced by the following process.

In an aqueous medium, diethylenetriaminepentaacetic acid (DTPA) is allowed to react with water-soluble ruthenium (III) salt such as a hydrate of ruthenium (III) chloride. In this reaction system, since DTPA is nearly insoluble in water and the hydrate of ruthenium (III) chloride is water-soluble, the reaction between them is a solid-liquid reaction. The ruthenium salt used herein is not limited, as long as it is water-soluble. Preferable are ruthenium halides, particularly ruthenium (III) chloride and ruthenium (III) bromide, in view of solubility and reactivity with DTPA.

The reaction may be conducted at a reaction temperature of 600° C. to the boiling point, more preferably from 80 to 100° C. The reaction system does not have limitation on its concentration, as long as it does not cause a difficulty of stirring the suspension. However, since it is likely that the viscosity of the suspension increases in the end half of the reaction, it is desirable that the concentration of the solid is adjusted to 10 to 20 mass %. The reaction time, which is also not limited, is generally set to 30 minutes to 5 hours.

The solid phase produced by the solid-liquid reaction has light yellow to light green color. Since the solid phase has the extremely poor solubility to water, the resultant reaction liquid becomes slurry. The slurry is subjected to a solid-liquid separation such as filtration and centrifugation, to obtain only the solid phase.

The obtained solid phase is then dissolved into aqueous ammonia and the resulting solution is adjusted to pH 5 or more, preferably from pH 5.5 to pH 7.5, thereby obtaining $DTPA.Ru.(NH_4)_2$, which is the objective compound of the present invention. pH is adjusted by the concentration or the amount of the aqueous ammonia, or the amount of ammonia gas blown into the aqueous ammonia. Since pH of $DTPA.Ru.(NH_4)_2$ aqueous solution itself is about 5, when pH of the system is adjusted to 5 or more, the objective compound dissolved can be obtained in the aqueous solution containing excess ammonia.

Subsequently, the aqueous ammonia solution is concentrated under reduced pressure. In the concentration process, the excess ammonia is removed, and $DTPA.Ru.(NH_4)_2$ begins to crystallize as the hydrate(generally dihydrate) thereof after exceeding the saturation solubility thereof. The above-mentioned processes of the solid-liquid reaction and dissolution reaction into aqueous ammonia are desirably performed at a temperature of 500° C. or lower, from the view points of holding high reaction rate and suppressing decomposition reaction.

The crystals obtained by removing excess ammonia and water from the aqueous solution in the concentration process under reduced pressure are collected by the filtration, followed by washing with methanol or the like and drying, to obtain the hydrate of $DTPA.Ru.(NH_4)_2$ of light yellow crystals.

Preferable reduced pressure in the concentration process is 50 to 150 mmHg at 30 to 60° C. from the viewpoints of suppressing decomposition reaction and improving the efficiency of the concentration. In order to crystallize the objective compound, the concentration under reduced pressure and cooling crystallization processes may be effectively combined.

In most cases, the objective compound can be crystallized as the hydrate, usually as the dihydrate, as described above, although number of crystal water of the hydrate varies depending on conditions for crystallization, washing and drying. In addition, it is, of course, possible to obtain the objective compound as anhydride, depending on the drying conditions after the crystallization.

The inventive diammonium ruthenium diethylenetriaminepentaacetate produced in the above-mentioned manner is not decomposed in the aqueous solution as well as in the atmospheric condition and therefore can be stably preserved. Moreover, since the objective compound has an extremely high solubility to water, it can be stably stored in an aqueous solution without precipitating, even when acid or alkali is added to in the aqueous solution in order to change pH thereof.

The diammonium ruthenium diethylenetriaminepentaacetate produced in the above-mentioned manner can be effectively used, for example, as a catalyst for synthesizing ammonia, as a hydrogenation catalyst for carbonyl compounds or aromatic compounds and, in addition, as a raw material for producing ruthenium-base metal oxide ceramics.

EXAMPLES

The present invention will be illustrated with reference to several examples below, which are not intended to limit the scope of the invention. Modifications and variations can be made without departing from the purpose described hereinabove and hereinafter and all such modifications and variations are also included in the technical scope of the present invention.

EXAMPLE 1

In a 500 ml beaker, 32.65 g (0.081×1.02 mole) of diethylenetriaminepentaacetic acid and 19.71 g (0.081 mole) of n hydrates of ruthenium (III) chloride (ruthenium content: 41.8%) were added with water so as to obtain a mixture liquid having a total weight of 400 g. These compounds were allowed to react with each other at a liquid temperature of 100° C. for 1 hour with stirring the liquid mixture, to obtain slurry. The reaction ratio was 98%. The obtained slurry was cooled to 10° C. and filtered to remove insoluble matter therefrom. The insoluble matter was washed sufficiently with water, to give a light yellow wet cake.

The cake was put in a 500 ml beaker containing 80 g of water, and then 15 g of aqueous ammonia was added therein.

Consequently, pH of the liquid became 7.1 and the cake was completely dissolved. Subsequently, this solution was filtered to remove insoluble matter therefrom, followed by the concentration under a reduced pressure of 100 mmHg to vaporize about 100 g of water. The crystals separated were removed from the solution by filtering. The removed crystals were washed with a mixed medium of water and methanol (water:methanol=1:5), to obtain 10.2 g of yellow crystals of DTPA.Ru(III).(NH$_4$)$_2$.2H$_2$O. The yield was 22% and the obtained crystals have the following properties:

- molecular weight: 561.07 (dihydrate salt)
- pH of 5% aqueous solution: 5.10
- solubility (25° C.): 53%
- melting point: 265° C. (decomposition)
- infrared absorption spectrum (KBr): FIG. 1
- chart of differential thermal analysis (thermogram): FIG. 2
- Ruthenium content: 17.9%

The above Ruthenium content was 99.53% with respect to the calculated value using the theoretical molecular weight. The difference between actual and calculated values was within the range of experimental error.

INDUSTRIAL APPLICABILITY

The present invention is configured as above, thus it is possible to provide a novel crystalline compound of diammonium ruthenium diethylenetriaminepentaacetate which is water-soluble and stable both in the air and the aqueous solution. The novel compound is effectively used as a catalyst for ammonia synthesis, a hydrogenation catalyst for carbonyl compounds, aromatic compounds, in addition, as a raw material for producing ruthenium-base metal oxide ceramics.

What is claimed is:

1. Diammonium ruthenium diethylenetriaminepentaacetate represented by formula (1) or a hydrate thereof

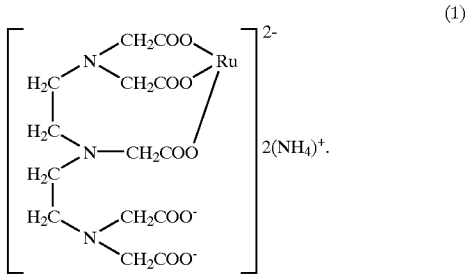

2. A process for producing diammonium ruthenium diethylenetriaminepentaacetate comprising:
    conducting a solid-liquid reaction between diethylenetriaminepentaacetic acid and water-soluble ruthenium salt in an aqueous medium to obtain slurry;
    subjecting the slurry to a solid-liquid separation to remove a solid phase portion therefrom; and
    dissolving the solid phase portion into aqueous ammonia.

3. A process for producing diammonium ruthenium diethylenetriaminepentaacetate according to claim 2, further comprising crystallizing a hydrate of diammonium ruthenium diethylenetriaminepentaacetate from a solution obtained by dissolving the solid phase portion into the aqueous ammonia, to obtain crystals of the hydrate thereof.

4. A process for producing diammonium ruthenium diethylenetriaminepentaacetate, comprising drying the hydrate of the claim 3 by heating to obtain an anhydride of the diammonium ruthenium diethylenetriaminepentaacetate.

* * * * *